United States Patent
Hristov et al.

(10) Patent No.: US 12,201,512 B2
(45) Date of Patent: Jan. 21, 2025

(54) DELIVERY SLEEVE

(71) Applicant: MENTOR WORLDWIDE LLC, Irvine, CA (US)

(72) Inventors: Krasimira Hristov, Hillsborough, NJ (US); Marc Feinberg, Ringoes, NJ (US); Leo Kriksunov, Ithaca, NY (US); Robert Tannhauser, Bridgewater, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 0 days.

(21) Appl. No.: 15/913,463

(22) Filed: Mar. 6, 2018

(65) Prior Publication Data
US 2019/0274818 A1    Sep. 12, 2019

(51) Int. Cl.
*A61F 2/12*      (2006.01)
*A61B 17/34*     (2006.01)
*A61M 25/00*     (2006.01)

(52) U.S. Cl.
CPC ............ *A61F 2/12* (2013.01); *A61B 17/3468* (2013.01); *A61M 25/0054* (2013.01); *A61B 17/3417* (2013.01); *A61B 17/3462* (2013.01)

(58) Field of Classification Search
CPC ........................................ A61F 2/12
See application file for complete search history.

(56) References Cited

U.S. PATENT DOCUMENTS

| | | |
|---|---|---|
| 4,035,850 A | 7/1977 | Cresswall |
| 4,955,906 A | 9/1990 | Coggins et al. |
| 5,201,779 A | 4/1993 | Shiao |
| 5,279,539 A | 1/1994 | Bohan et al. |
| 5,549,679 A | 8/1996 | Kuslich |
| 5,723,006 A | 3/1998 | Ledergerber |
| 5,728,065 A | 3/1998 | Follmer et al. |
| 6,467,612 B1 | 10/2002 | Rosenfeld |

(Continued)

FOREIGN PATENT DOCUMENTS

| | | |
|---|---|---|
| CN | 2897165 Y | 5/2007 |
| CN | 208552129 U | 3/2019 |

(Continued)

OTHER PUBLICATIONS

PCT Notification of Transmittal of the International Search Report and International Search Report of International Application No. PCT/IB2019/051820 Dated Jun. 18, 2019, 8 Pages.

(Continued)

*Primary Examiner* — Jerrah Edwards
*Assistant Examiner* — Christine L Nelson
(74) *Attorney, Agent, or Firm* — Etan S. Chatlynne; Calderon Safran & Wright P.C.

(57) ABSTRACT

An implant delivery sleeve is disclosed. The sleeve may comprise a first tube including a first segment, a second segment, and a third segment. The first segment may have a first stiffness, the second segment may have a second stiffness, and the third segment may have a third stiffness. The third stiffness may be greater than the second stiffness and the second stiffness may be greater than the first stiffness. The implant-delivery sleeve may be used to deliver a breast implant to a subject. The implant may be deformed within the sleeve, to advance it within the sleeve and extrude it from the distal end of the sleeve.

13 Claims, 8 Drawing Sheets

(56) References Cited

U.S. PATENT DOCUMENTS

| | | |
|---|---|---|
| 6,605,093 B1 | 8/2003 | Blake |
| 8,070,768 B2 | 12/2011 | Kim et al. |
| 8,182,459 B2 | 5/2012 | Dann et al. |
| 8,187,297 B2 | 5/2012 | Makower et al. |
| 8,211,173 B2 | 7/2012 | Keller et al. |
| 8,409,279 B2 | 4/2013 | Freund |
| 8,641,758 B1 | 2/2014 | Anderson et al. |
| 8,993,831 B2 | 3/2015 | Sharma et al. |
| 9,414,941 B2 | 8/2016 | Placik et al. |
| 10,105,213 B2* | 10/2018 | Weinzweig ............... A61F 2/12 |
| 10,842,602 B2 | 11/2020 | Alexander et al. |
| 11,324,581 B2 | 5/2022 | Heneveld |
| 11,452,511 B2 | 9/2022 | Barbot et al. |
| 11,690,614 B2 | 7/2023 | Gross et al. |
| 11,690,716 B2 | 7/2023 | Hosmer et al. |
| 11,712,345 B2 | 8/2023 | Olmos et al. |
| 11,723,769 B2 | 8/2023 | Basude et al. |
| 2002/0091443 A1 | 7/2002 | Yoon |
| 2004/0225278 A1* | 11/2004 | Poole ................ A61M 25/0051 |
| | | 604/523 |
| 2005/0080430 A1 | 4/2005 | Wright et al. |
| 2007/0276484 A1 | 11/2007 | Abell et al. |
| 2008/0167606 A1* | 7/2008 | Dann ............. A61M 25/09041 |
| | | 604/95.04 |
| 2009/0030400 A1 | 1/2009 | Bose et al. |
| 2009/0204107 A1 | 8/2009 | Keller et al. |
| 2011/0082546 A1 | 4/2011 | Freund |
| 2011/0144688 A1 | 6/2011 | Reiss et al. |
| 2014/0148901 A1 | 5/2014 | Anderson et al. |
| 2014/0228951 A1 | 8/2014 | Zochowski |
| 2014/0249510 A1 | 9/2014 | Koblish et al. |
| 2014/0350462 A1* | 11/2014 | Ataollahi ............. A61B 1/3132 |
| | | 604/95.04 |
| 2015/0032208 A1 | 1/2015 | Preissman |
| 2016/0095733 A1 | 4/2016 | Sharma et al. |
| 2016/0374720 A1 | 12/2016 | Anderson et al. |
| 2017/0007295 A1 | 1/2017 | Geisz |
| 2017/0020500 A1 | 1/2017 | Taylor et al. |
| 2017/0303905 A1 | 10/2017 | Wilson |
| 2018/0116779 A1 | 5/2018 | Marx |
| 2018/0126119 A1* | 5/2018 | McNiven ............ A61M 25/005 |
| 2019/0274817 A1 | 9/2019 | Hristov |
| 2019/0274819 A1 | 9/2019 | Graf et al. |
| 2019/0343620 A1 | 11/2019 | Mlodinow et al. |
| 2020/0222174 A1 | 7/2020 | Rosenberg |
| 2021/0052359 A1 | 2/2021 | Heneveld |
| 2021/0244527 A1 | 8/2021 | Heneveld |
| 2022/0000604 A1 | 1/2022 | Graf et al. |
| 2022/0054254 A1 | 2/2022 | Gryskiewicz et al. |
| 2022/0233297 A1 | 7/2022 | Heneveld |
| 2023/0060747 A1 | 3/2023 | Marks et al. |
| 2023/0098318 A1 | 3/2023 | Hristov et al. |
| 2023/0255608 A1 | 8/2023 | Sarna et al. |

FOREIGN PATENT DOCUMENTS

| | | |
|---|---|---|
| EP | 2 630 927 A2 | 8/2013 |
| WO | 2010/099541 A1 | 9/2010 |
| WO | 2010/126462 A1 | 11/2010 |
| WO | 2012/177587 A1 | 12/2012 |
| WO | 2017/213716 A1 | 12/2017 |
| WO | 2019/171300 A1 | 9/2019 |

OTHER PUBLICATIONS

Shaa'ista Ameen, 'No Touch' Breast-Implant Insertion Device, Submitted To the University of Cape Town, Faculty of Health Sciences, Department of Human Biology, University of Cape Town, Date of Submission: Jan. 1, 2016, URL: https://open.uct.ac.za/bitstream/handle/11427/20491/thesis_hsf_2016_ameen_shaa_039_ista.pdf?sequene=1 [retrieved on Feb. 27, 2018], pp. 74-76.

PCT Notification of Transmittal of the International Search Report and the Written Opinion of the International Searching Authority, or the Declaration for International Application No. PCT/IB2021/055927 dated Oct. 4, 2021, 6 pages.

\* cited by examiner

DELIVERY SLEEVE

CROSS-REFERENCE TO CO-PENDING APPLICATIONS

This application is a counterpart of U.S. patent application Ser. No. 15/913,438, filed Mar. 6, 2018, and Ser. No. 15/913,484, filed Mar. 6, 2018, which are incorporated by reference herein in their entirety.

FIELD

The subject matter disclosed herein relates to devices and methods for delivering implants into a subject.

BACKGROUND

Tapered flexible sleeves, such as that marketed under the brand name, KELLER FUNNEL®, may be used as a delivery device for implanting a silicone-gel breast implant into a subject. These sleeves permit delivery of the implant through an incision that is shorter than it would need to be if the sleeve were not used. These sleeves may also lower the likelihood of introducing contaminants, e.g., microorganisms, into the subject through the incision because they minimize the amount of contact between the implant, surgeon's hands, and subject's tissue.

SUMMARY

An implant delivery sleeve is disclosed. The sleeve may comprise a first tube including a first segment, a second segment, and a third segment. The first segment may have a first stiffness, the second segment may have a second stiffness, and the third segment may have a third stiffness. The third stiffness may be greater than the second stiffness and the second stiffness may be greater than the first stiffness. A hoop may be attached to a proximal end of the first tube.

In some embodiments, the first segment of the first tube may include a second tube disposed about the first tube, the second segment may include a third tube disposed about the first tube, and the third segment may include a fourth tube disposed about the first tube. Each of the first tube, the second tube, the third tube, and the fourth tube may be made from an elastomeric rubber.

In some embodiments, the implant-delivery sleeve may also include perforations disposed through the first tube. A greater number of perforations may be disposed through the first segment than the second segment. Further, a greater number of perforations may be disposed through the second segment than the third segment.

In some embodiments the first tube may have a frusto-conical configuration. In some embodiments, the sleeve may include a mesh. For example, the second tube may be fabricated from a mesh.

The implant-delivery sleeve may be used to deliver an implant, e.g., a silicone-gel breast implant, to a subject, e.g., a human patient, according to the following method and variations. First, the implant may be provided. The implant may be inserted into the first segment of the sleeve. At least a portion of the third segment may be positioned proximate to an incision in the subject and then within a tissue pocket of the subject. The implant may be deformed within the sleeve, to advance it within the sleeve and extrude it from the distal end of the sleeve. Finally, the portion of the third segment may be withdrawn from the tissue pocket.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
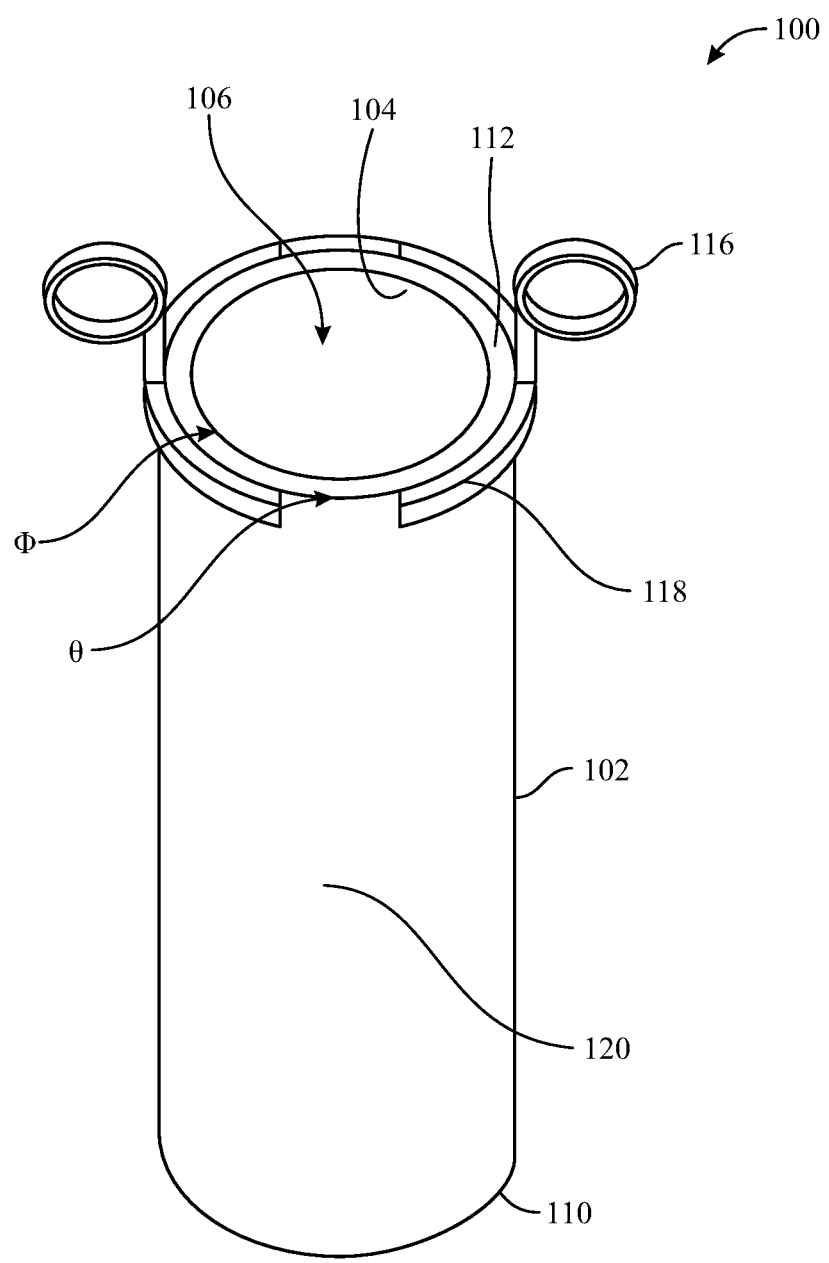
FIG. 1 depicts a delivery sleeve.

FIG. 1 shows an exemplary embodiment of a delivery sleeve 100. Sleeve 100 has a hollow cylindrical, or tubular, form. Specifically, sleeve 100 may include an outer surface 102 having an outer diameter $\theta$ and an inner surface 104 having an inner diameter $\varphi$. Inner diameter $\varphi$ is constant along the entire length of sleeve 100 such that inner surface 104 defines a passage 106 having a uniform circular profile through sleeve 100. Thus, sleeve 100 may be a tube 120.

Sleeve 100 may be used to deliver an implant, such as a breast implant, into a subject, such as a human patient. Breast implants typically have a diameter ranging from between approximately three inches and seven inches. Implants are typically referred to by their diameter, e.g., "a five-inch implant," and such diameters correspond to a diameter of the widest cross section of the implant that is parallel to the base of the implant. Silicone-gel implants are flexible and pliable, and may be squeezed considerably to constrain the implant in a configuration such that the diameter of the implant may be constricted considerably, e.g., on the order of between approximately 2 times and 10 times. For example, if the implant is a "three-inch implant" the portion that is three inches may be squeezed to constrict that portion to having a width of approximately 1.5 inches. Once the constrictive forces are removed, the portion recovers its original shape having a three-inch diameter. Due to the flexible nature of silicone-gel implants, an implant may be squeezed through constrictions that are substantially smaller than the implant. Accordingly, inner diameter $\varphi$ of sleeve 100 may be between one half to one fifth of the implant's size. For example, the inner diameter φ may be approximately 1.5 inches. Outer diameter θ need not be constant. Accordingly, at distal end 110, θ may approximate or be smaller than the length of an incision for inserting the implant, e.g., between approximately one inch and five inches. In some embodiments, φ may be between approximately 1 inch and 1.5 inches and θ at the distal end may be between approximately two inches and four inches. For example, φ may be approximately one inch and θ at distal end 110 may be approximately three inches.

In some embodiments, the wall thickness of sleeve 100 may be defined as a difference between outer diameter θ and inner diameter φ of sleeve 100, divided by two. The wall thickness of sleeve 100 may range from about 0.01 inches to 0.25 inches. For example, the wall thickness may of sleeve 100 may be equal to approximately 0.05, 0.07, 0.1, 0.12, 0.15, or 0.2 inches. The wall thickness may be uniform along sleeve 100, or it may vary. In some embodiments, the inner diameter φ remains constant.

Sleeve 100 may be fabricated from a material that may be elastically or plastically deformed, e.g., an elastomer such as silicone rubber, such that when an implant is passed therethrough, outer diameter θ and inner diameter φ may be enlarged or dilated. Thus sleeve 100 may conform to the shape of an implant being passed therethrough, which implant may itself be in a state of deformation caused by the sleeve.

In some embodiments, the stiffness of sleeve 100 may be different at distal end 110 and proximal end 112 such that the force required to deform sleeve 100 may be different at distal end 110 and proximal end 112. For example, a lesser force may generate the same amount of strain at proximal end 112 than a greater force may generate at distal end 102. In various embodiments, proximal end 112 may be flexible and distal end 110 may be stiffer than proximal end 112. For example, distal end 110 may be rigid. In some embodiments, the stiffness may change along the length of sleeve 100 between proximal end 112 and distal end 110. In various embodiments, the stiffness of sleeve 100 may be a function of position along sleeve 100.

In some embodiments, sleeve 100 is constructed such that its stiffness at the proximal end is less than or equal to the stiffness at other locations along the length of sleeve 100, whereas its stiffness at the distal end is greater than or equal to the stiffness at other locations along the length of sleeve 100. Specifically, in some embodiments, upon advancement of the implant through distal end 110, the distal end is sufficiently stiff such that the distal end may not dilate or may dilate from approximately 0% to 15% of either outer diameter θ or inner diameter φ, for example, approximately 3%, 5%, or 10%. In some embodiments, proximal end 112 is sufficiently flexible or elastic such that it may dilate to readily accept insertion of the implant therein. For example, dilation of the proximal end may be approximately 30% to 300% of either outer diameter θ or inner diameter φ of sleeve 100, such as dilation of approximately 40%, 50%, 75%, 100%, 150%, 200%, 250%. A dilation mechanism, such as hoops 116 shown in FIG. 1, may be incorporated onto proximal end 112 to assist in handling sleeve 100. Hoops 116 may include an arcuate structure 118 attached thereto. Accordingly, hoops 116 may be subject to opposing forces by a user, e.g., by pulling hoops 116 away from each other, which causes proximal end 112 to dilate (i.e., increases inner diameter φ), and perhaps elongate, which in turn facilitates introduction of an implant therein. Hoops 116 may be fabricated from a rigid plastic, such as polycarbonate, or a metal, such as stainless steel.

Figure 2:
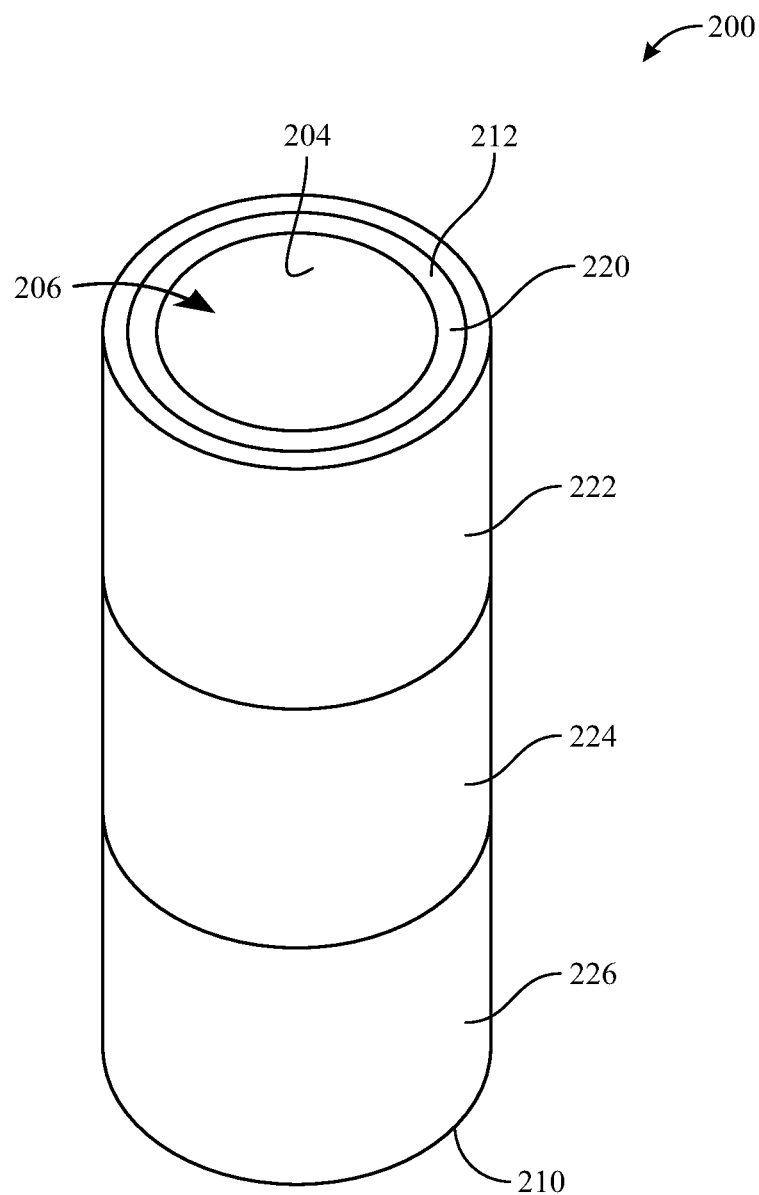
FIG. 2 depicts a first alternative embodiment of a delivery sleeve.

Varying stiffness of a delivery sleeve may be provided by various designs. For example, FIG. 2 shows sleeve 200, which comprises a first tube 220, a second tube 222, a third tube 224, and a fourth tube 226. Second tube 222 may be disposed about and attached (e.g., bonded with silicone glue) to first tube 220 proximate to proximal end 212. Fourth tube 226 may be disposed about and attached to first tube 220 at or proximate to distal end 210. Third tube 224 may be disposed about and attached to first tube 220 between second tube 222 and fourth tube 226. Each tube 220, 222, 224, and 226 may be flexible, e.g., an elastomer such as silicone rubber, but have a different stiffness, as determined by, e.g., tubing thickness and/or durometer. For example, first tube 220 may have a thickness of between approximately 0.01 inches and 0.02 inches, and a shore A durometer between approximately 10 and 15; second tube 222 may have a thickness of between approximately 0.02 inches and 0.03 inches, and a shore A durometer between approximately 15 and 20; third tube 224 may have a thickness of between approximately 0.03 inches and 0.04 inches, and a shore A durometer between approximately 20 and 30; and fourth tube 226 may have a thickness of between approximately 0.04 inches and 0.05 inches, and have a shore A durometer between approximately 30 and 40. In various embodiments, the hardness or durometer of tubes 222, 224, and 226 are equal, however the thickness of tube 226 is greater than the thickness of tube 224 and the thickness of tube 224 is greater than the thickness of tube 222. In various embodiments, the thickness of tubes 222, 224, and 226 are equal, however the durometer of tube 226 is greater than the durometer of tube 224 and the durometer of tube 224 is greater than the durometer of tube 222. Accordingly, sleeve 200 may have three different stiffnesses along its length, with the stiffness increasing from proximal end 212 toward distal end 210. In some designs, second tube 222 need not be utilized to fabricate a sleeve having three different stiffnesses along its length so long as first tube 220 has a shore A durometer between approximately 10 and 40. In some designs proximal end 212 of first tube 220 extends above second tube 222 to provide a segment of sleeve 200 that has a stiffness that is less than those portions of sleeve 200 distal to this segment. In some embodiments, a rigid ring, such as a polycarbonate or stainless steel ring, may be incorporated onto distal end 210 such that distal end 210 is stiff and not flexible. In some embodiments, the degree of stiffness gradually increases from proximal end 212 toward distal end 210.

Figure 3A:
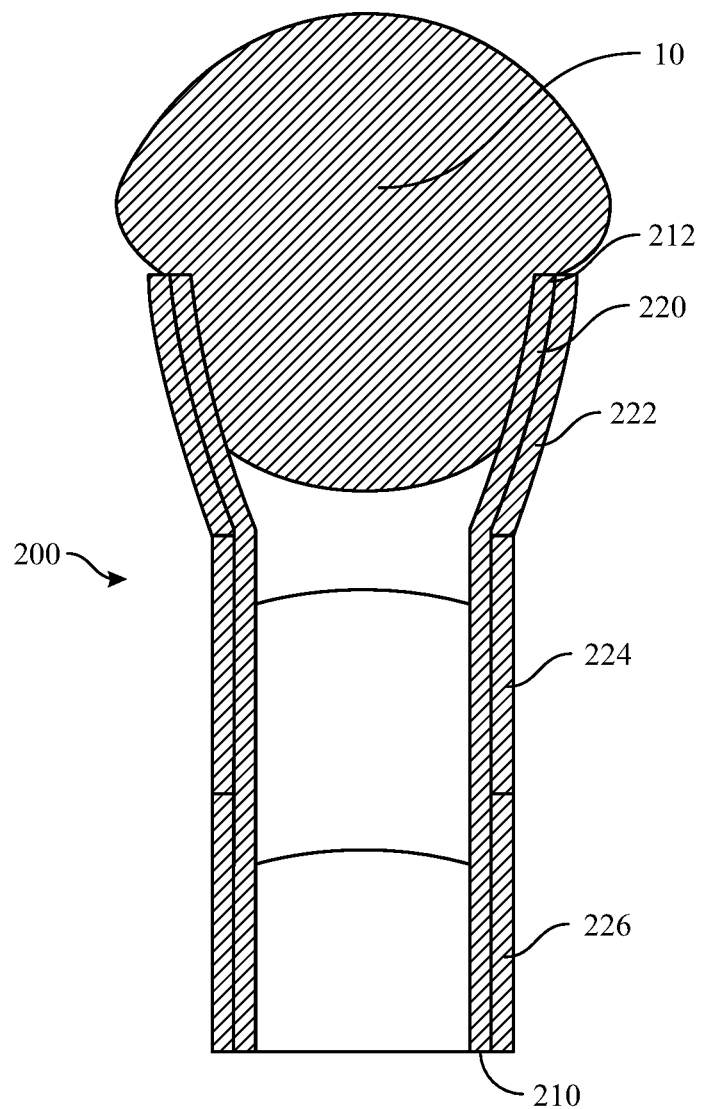
FIG. 3A depicts the first alternative embodiment of the delivery sleeve of FIG. 2 with an implant disposed therein, proximate to the proximal end of the sleeve.
Figure 3B:
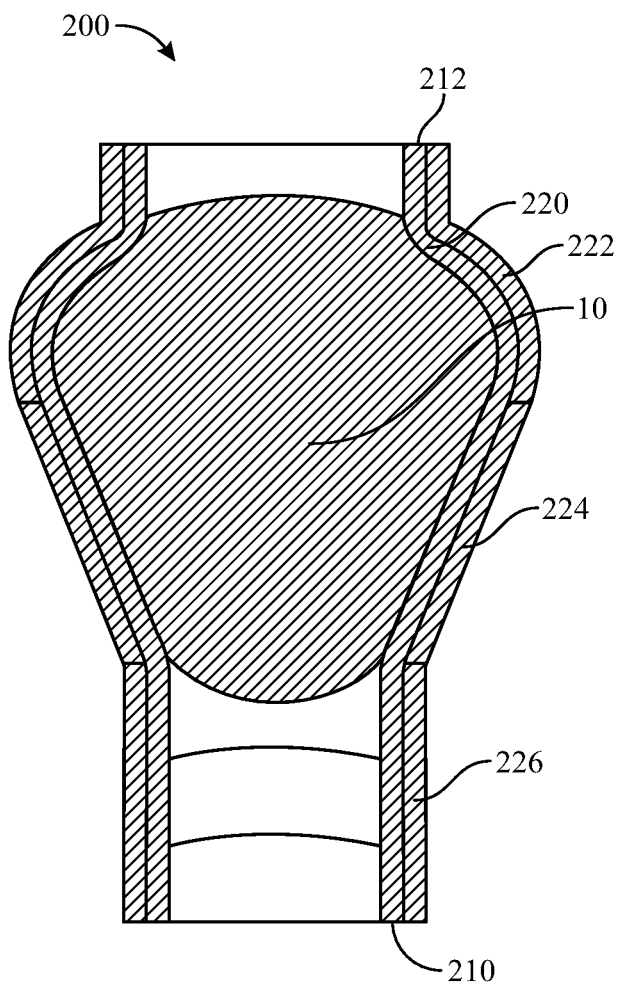
FIG. 3B depicts the first alternative embodiment of the delivery sleeve of FIG. 2 with the implant disposed therein, proximate to the middle of the sleeve.
Figure 3C:
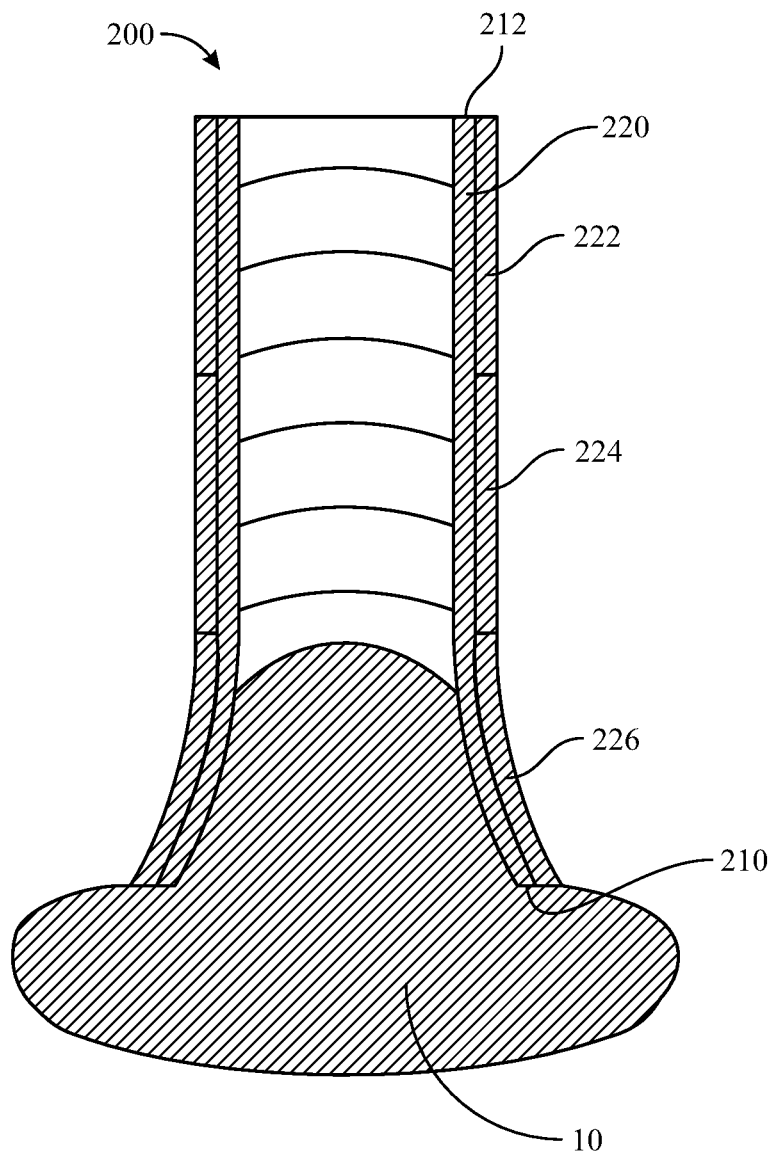
FIG. 3C depicts the first alternative embodiment of the delivery sleeve of FIG. 2 with the implant disposed therein, proximate to the distal end of the sleeve.

FIGS. 3A, 3B, and 3C show a cross-section view of sleeve 200 with implant 10 disposed at various positions therein. In FIG. 3A, implant 10 is disposed proximate to proximal end 212, partially within a segment of first tube 220 that is surrounded by second tube 222. Implant 10 is compressed within first tube 220 and first tube 220 is stretched by implant 10. In FIG. 3B, implant 10 is disposed proximate to the middle of sleeve 200, within a segment of first tube 220 that is surrounded by second tube 222 and third tube 224. Implant 10 is compressed within first tube 220 more that it was in FIG. 3A because third tube 224 is stiffer than second tube 222. Correspondingly, third tube 224 in FIG. 3B is stretched less than second tube 222 in FIG. 3A. A portion of sleeve 200 proximate to proximal end 212 is no longer stretched because implant 10 is not disposed therein. In FIG. 3C, implant 10 is shown partially extruded from distal end 210, partially within a segment of first tube 220 that is surrounded by fourth tube 226. Implant 10 is compressed within first tube 220 more so than it was in FIG. 3B because fourth tube 226 is stiffer than third tube 224. Correspondingly, fourth tube 226 in FIG. 3C is stretched less than third tube 224 in FIG. 3B. The segments of sleeve 200 including second tube 222 and third tube 224 are no longer stretched because implant 10 is not disposed therein.

In some embodiments, a number of tubes greater than three tubes, each having a different stiffness, may be disposed about and attached to first tube 220. For example, between four and fifty tubes may be disposed about and attached to first tube 220 in a manner whereby the stiffness of these tubes increases from proximal end 212 to distal end 210. Accordingly, when ten tubes are used, sleeve 200 may have ten different stiffnesses along its length (or eleven stiffnesses if a proximal segment of first tube 220 extends above the other tubes), with the stiffness increasing from proximal end 212 toward distal end 210. Thus, the stiffness of sleeve 200 may be increased gradually instead of abruptly, from proximal end 212 toward distal end 210.

By deforming implant 10 into a long and narrow shape that conforms to passage 206 as passage 206 conforms to implant 10, sleeve 200 may be used to shape implant 10 into a form, such as an elongated form, that can readily pass through an incision and into a tissue pocket of a subject. Accordingly, a surgeon may use a delivery sleeve, such as sleeve 200, according to the following steps. First, implant 10 (e.g., a breast implant) and sleeve 200 may be provided. Second, implant 10 may be inserted into first tube 220 through proximal end 212. Third, implant 10 may be advanced from proximal end 212 in a direction toward distal end 210. A user may squeeze sleeve 200 or push a tool against implant 10 through passage 206 to apply a force to implant 10 that is parallel to a longitudinal axis of sleeve 200 and directed toward distal end 210. Fourth, sleeve 200 may be deformed or dilated by implant 10 passing therethrough. Fifth, implant 10 may be deformed into a shape having a diameter that is smaller than an incision, which may or may not be stretched by the implant and sleeve. Sixth implant 10 may be extruded from sleeve 200 via distal end 210. Seventh, implant 10 may be disposed within a tissue pocket of a subject. It may be desirable to lubricate implant 10 and/or the inside of sleeve 200, i.e., inner surface 204, to facilitate advancement of implant 10 through sleeve 200.

Alternative designs may also impart varying stiffness to a delivery sleeve. For example, second tube 222, third tube 224, and fourth tube 226 may be fabricated from flexible mesh, comprised of, e.g., polypropylene or polyester, instead of an elastomer. The weave of each mesh tube may impart an increasing amount of stiffness to sleeve 200. That is, the closer each mesh tube is to distal end 210, the stiffer it is, and the further each mesh tube is from distal end 210, the more flexible it is. The stiffness within each mesh tube may also vary. For example, the mesh may have a substantially uniform thickness throughout sleeve 200 and have an anisotropic knitted or woven structure that has a greater stiffness in a first direction (e.g., towards distal end 210) than in a second direction (e.g., circumferentially about sleeve 200). Further, the density or tightness of the knit may be increased from the proximal end to the distal end of the tube, providing for greater stiffness at the distal end than the proximal end.

Figure 4:
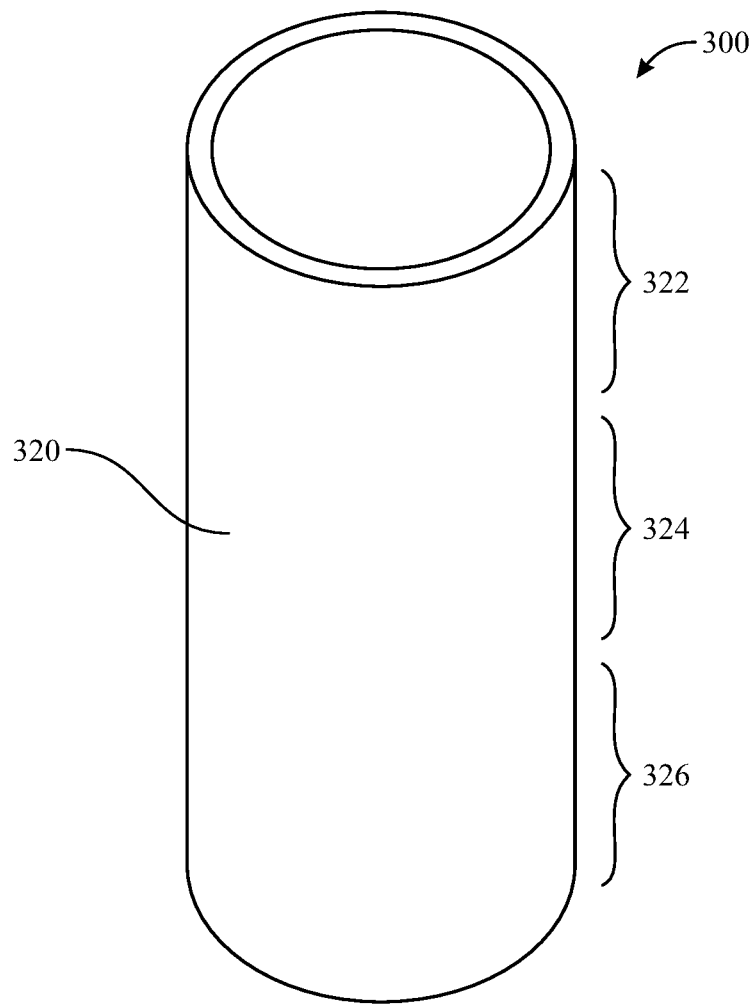
FIG. 4 depicts a second alternative embodiment of a delivery sleeve.

In alternative designs, a delivery sleeve may include a single elastomeric tube. For example, FIG. 4 shows delivery sleeve 300, which is comprised of a single tube 320 having a first segment 322, a second segment 324, and a third segment 326. First segment 322 may have a shore A durometer between approximately 10 and 20; second segment 324 may have a shore A durometer between approximately 20 and 30; and third segment 326 may have a shore A durometer between approximately 30 and 40. Such stiffnesses may be imparted to tube 320 by imparting differing degrees of cross linking to the material forming the sleeve. For instance, heating delivery sleeve 300 and exposing portions to various amounts of catalyst may increase the amount of cross-linking and thus decrease elasticity.

Alternatively, such stiffnesses may be imparted to tube 320 by irradiating the material that forms the sleeve. For example, the material (e.g., silicone rubber) may be irradiated (e.g., via gamma radiation), which may induce changes in the molecular architecture of the material, resulting in an increase in molecular weight, an increase in stiffness, and/or a decrease in elasticity.

Figure 5:
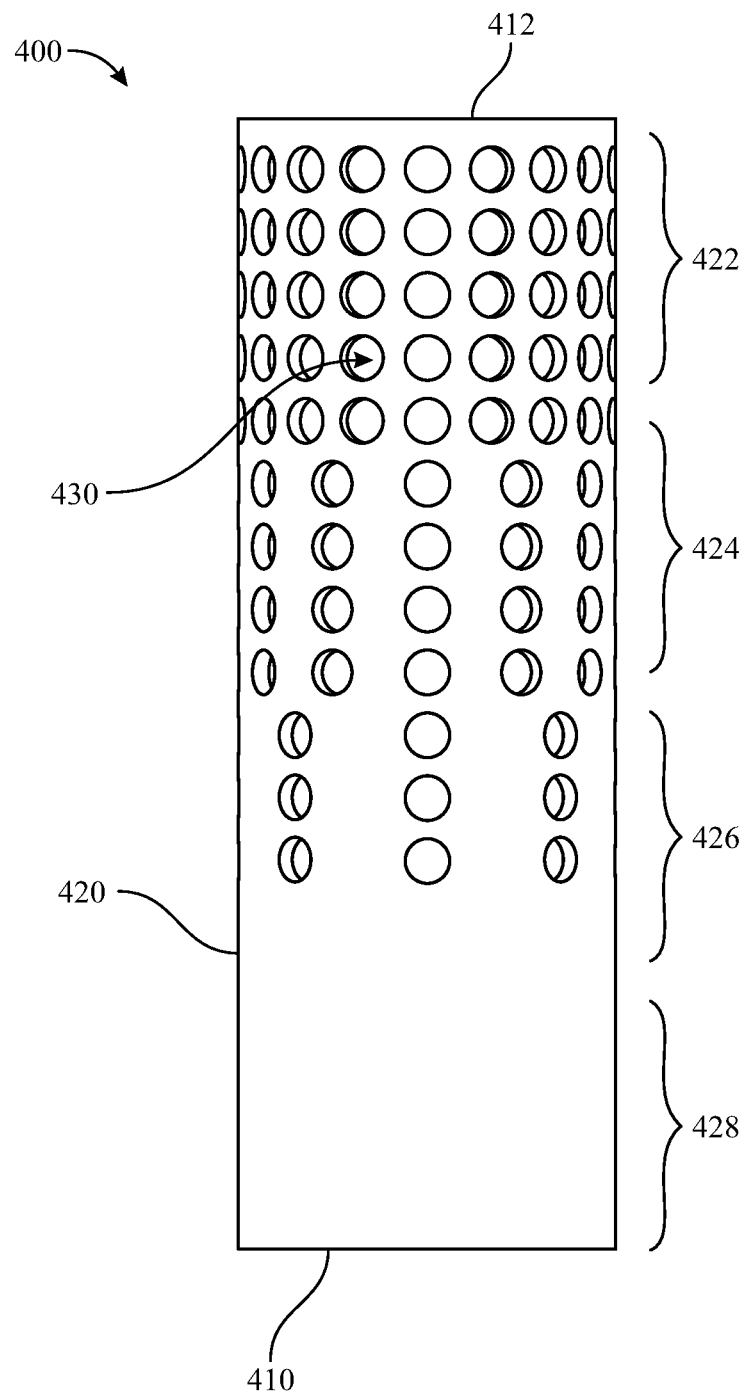
FIG. 5 depicts a third alternative embodiment of a delivery sleeve.

Alternatively, such stiffnesses may be imparted by removing material from a tube of a sleeve. With reference to FIG. 5, sleeve 400 comprises a tube 420 having a proximal end 412, a distal end 410, a first or proximate segment 422, a second segment 424, a third segment 426, and a fourth or distal segment 428. Various perforations or holes 430 may be disposed through tube 420 such that the greater the number of holes 430 over a given area, the more flexible the tube is over that area. Segments 422, 424, 426, and 428 may each include or exclude perforations 430 therethrough to achieve a desired stiffness and/or elasticity profile along sleeve 400. For example, as shown, segment 422 includes the greatest number of perforations (e.g., between approximately 50 and 100 perforations), segment 424 includes fewer perforations than segment 422 but more perforations than segment 426 (e.g., between approximately 20 and 50 perforations), segment 426 includes more perforations than segment 428 (e.g., between approximately 5 and 20 perforations) and segment 428 does not include any perforations. Thus, the elasticity of sleeve 400 increases from proximal end 412 toward distal end 410, over each of the segments, as a function of the number of perforations through each segment. Perforations 430 may have any suitable shape or cross-section, e.g., elliptical, circular, rectangular, square, or any combination thereof.

Figure 6:
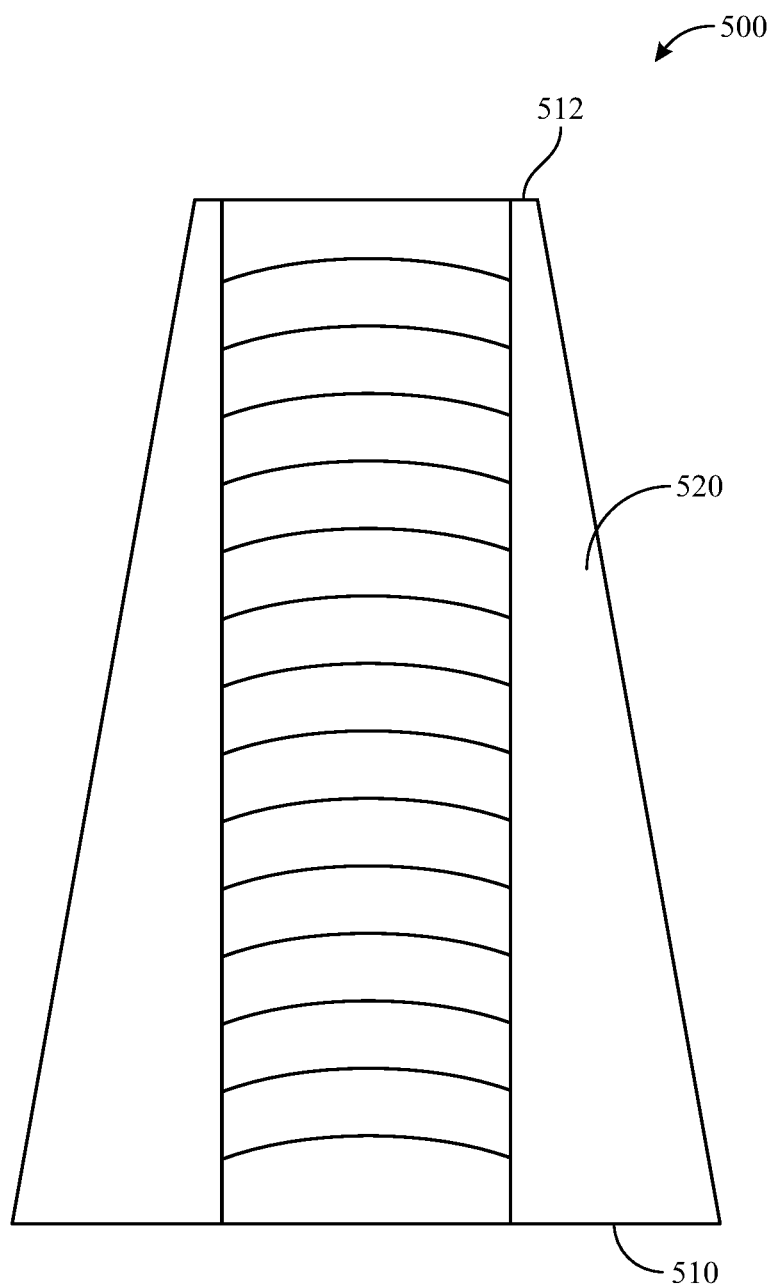
FIG. 6 depicts a fourth alternative embodiment of a delivery sleeve.

Alternatively, as shown in FIG. 6, sleeve 500, shown in cross-section, may include a first tube 520 that is thicker at distal end 510 than at proximal end 512. Thus, the entirety of first tube 520 may be fabricated from an elastomer having a shore A durometer of between approximately 10 and 40, but stiffness may vary as a function of thickness. For example, proximate to proximal end 512, the thickness of tube 520 may be between approximately 0.01 inches and 0.04 inches whereas proximate to distal end 510, the thickness of tube 520 may be between approximately 0.01 inches and 0.25 inches. Thus, first tube 520 may have a frustoconical configuration outside while having a internal cylindrical passage of uniform internal diameter, resulting in the stiffness of sleeve 500 gradually increasing from proximal end 512 to distal end 510. Tube 520 may be fabricated according to various techniques including machining, extrusion, dipping and/or molding, such as injection molding, liquid injection molding, or compression molding.

The stiffness provided by the various segments of delivery sleeves 100, 200, 300, 400 and 500 may be defined according to measurements of strain. For example, the inner diameter of the sleeve at the proximate end may dilate between approximately three times and ten times, whereas the inner diameter of the sleeve at the distal end may not dilate or may dilate up to approximately three times.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. An implant-delivery sleeve, comprising:
a first tube having a first stiffness;
a second tube disposed about the first tube and attached directly to the first tube, the second tube having a second stiffness;
a third tube disposed about the first tube and attached directly to the first tube, the third tube having a third stiffness; and
a fourth tube disposed about the first tube and attached directly to the first tube, the fourth tube having a fourth stiffness,
wherein the third stiffness is greater than the second stiffness and the second stiffness is greater than the first stiffness, and
wherein the third tube is disposed between the second tube and the fourth tube.

2. The implant-delivery sleeve of claim 1, further comprising a hoop attached to a proximal end of the first tube.

3. The implant-delivery sleeve of claim 1, wherein the first tube, the second tube, the third tube, and the fourth tube are made from an elastomeric rubber.

4. The implant-delivery sleeve of claim 1, further including perforations disposed through the first tube.

5. The implant-delivery sleeve of claim 4, wherein a greater number of perforations are disposed through the first segment than the second segment.

6. The implant-delivery sleeve of claim 5, wherein a greater number of perforations are disposed through the second segment than the third segment.

7. The implant-delivery sleeve of claim 1, wherein the first tube has a frustoconical configuration.

8. The implant-delivery sleeve of claim 1, wherein the sleeve includes a mesh.

9. The implant delivery sleeve of claim 8, wherein the second tube is fabricated from the mesh.

10. The implant-delivery sleeve of claim 1, wherein the first tube has a shore A durometer of between approximately 10 and approximately 15.

11. The implant-delivery sleeve of claim 10, wherein the second tube has a shore A durometer of between approximately 15 and approximately 20.

12. The implant-delivery sleeve of claim 11, wherein the third tube has a shore A durometer of between approximately 20 and approximately 30.

13. The implant-delivery sleeve of claim 12, wherein the fourth tube has a shore A durometer of between approximately 30 and approximately 40.

\* \* \* \* \*